United States Patent [19]

Hodge et al.

[11] 4,244,828

[45] Jan. 13, 1981

[54] LUBRICATING OIL COMPOSITION

[75] Inventors: John W. Hodge, Fishkill; Harry Chafetz, Poughkeepsie, both of N.Y.

[73] Assignee: Texaco Inc., White Plains, N.Y.

[21] Appl. No.: 960,517

[22] Filed: Nov. 13, 1978

[51] Int. Cl.$^3$ .............................................. C10M 1/48
[52] U.S. Cl. ........................... 252/46.7; 252/32.7 HC; 260/943; 260/984
[58] Field of Search ...................... 252/46.7, 32.7 HC; 260/943, 984

[56] References Cited

U.S. PATENT DOCUMENTS

| | | | |
|---|---|---|---|
| 2,883,339 | 4/1959 | Richardson | 252/32.7 HC |
| 2,911,371 | 11/1959 | Weis | 252/32.7 HC X |
| 3,042,613 | 7/1962 | Lemmon et al. | 252/32.7 HC |
| 3,087,956 | 4/1963 | Lacoste et al. | 252/49.8 |
| 3,133,022 | 5/1964 | Sabol et al. | 252/32.7 HC X |
| 3,235,497 | 2/1966 | Lee | 252/46.7 |
| 3,294,684 | 12/1966 | McNinch et al. | 252/32.7 HC X |
| 3,296,132 | 1/1967 | Petersen et al. | 252/32.7 HC X |
| 3,324,032 | 6/1967 | O'Halloran | 252/46.7 |

Primary Examiner—Andrew Metz
Attorney, Agent, or Firm—Carl G. Ries; Robert A. Kulason; James J. O'Loughlin

[57] ABSTRACT

An alkenethiophosphonic acid reaction product prepared by reacting an alkenethiophosphonic acid in which the alkene radical has a molecular weight in the range of 400 to 20,000 with a hydroxyalkyl carboxylic acid to form an intermediate reaction product, and reacting said intermediate reaction product with a polyamine, a polyol, or an alkanolamine to form said reaction product, and a lubricating oil composition containing said reaction product.

3 Claims, No Drawings

LUBRICATING OIL COMPOSITION

The invention relates to an alkenethiophosphonic acid reaction product prepared from an alkenethiophosphonic acid by reaction with a hydroxyalkyl carboxylic acid and a polyamine, a polyol or an alkanolamine, and to lubricating oil compositions comprising a mineral base oil and said reaction product as a dispersant.

Dispersants for lubricating oil compositions produced by the reaction of a polybutenethiophosphonic acid obtained from the reaction product of a polybutene of about 1200 molecular weight with $P_2S_5$ followed by hydrolysis with steam and ethoxylation with ethanol are known from U.S. Pat. No. 3,087,956, incorporated herein by reference. These products are obtained by reacting an alkenethiophosphonic acid with an alkene oxide, e.g., ethylene oxide or an alcohol, e.g., ethanol, to produce an alkenephosphonate having good detergent and dispersant properties in mineral base lubricating oil compositions.

Dispersants for lubricating oil composition produced by the reaction of an alkenesuccinic anhydride derived from a 1050 to 1400 molecular weight polybutene with an alkylamine or polyamine or polyol are also well known, and are disclosed, for example in U.S. Pat. Nos. 3,172,892; 3,272,746 and 3,381,022.

The invention as claimed herein provides an improved lubricant dispersant and improved mineral oil base motor oil compositions comprising a relatively high molecular weight reaction product of an alkenethiophosphonic acid with a hydroxyalkyl carboxylic acid, e.g., dialkylolpropionic acid, and a polyamine, polyol, or an alkanolamine. The alkenethiophosphonic acid reation product of the invention is effective as a dispersant in lubricating oil compositions prepared from mineral oil base stocks. An important property of this novel reaction product is that it is essentially ashless, i.e., it does not form ash deposits in the crankcase zone of an internal combustion engine. This property permits formulation of improved lubricating oil compositions which exhibit improved engine cleanliness and performance.

A novel alkenethiophosphonic acid reaction product is obtained by reacting an alkenethiophosphonic acid having the structural unit represented by the formula:

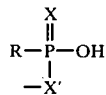

in which X and X' may be O or S and wherein an average of at least one is S and R is an alkene radical having an average molecular weight in the range from about 400 to about 20,000, preferably from about 750 to about 1,500 with, for example, dimethylolpropionic acid (DMP):

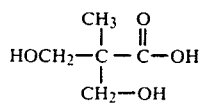

A most preferred alkenethiophosphonic acid starting reactant is one in which the alkene radical has an average molecular weight ranging from about 1050 to 1400 and a preferred hydroxyalkyl carboxylic acid is dimethylolpropionic acid.

The alkenethiophosphonic acid starting material is the reaction product of $P_2S_5$ with a long chain monoolefin followed by hydrolysis of the $P_2S_5$ reaction product with steam and extraction of the hydrolyzed product with methanol to remove low molecular weight acids of phosphorus. The olefinic reactant is obtained in the polymerization of a monoolefin according to known methods. Monoolefins having from two to six carbon atoms, such as ethylene, propylene, 1-butene, 2-butene, isobutene, amylene, hexylene, and mixtures thereof, are polymerized to produce monoolefinic polymers or copolymers having an average molecular weight within the desired range. The monoolefinic polymer or copolymer is then reacted with phosphorus pentasulfide in the presence of free sulfur and steam hydrolyzed to produce the alkenethiophosphonic acid employed in the production of the reaction products employed as dispersants in accordance with this invention. The procedures referred to are well known in the art, and are described for example in U.S. Pat. Nos. 3,087,956 and 3,969,235, and the processes involved do not constitute any part of the present invention.

A typical carboxylic acid reaction product obtained by reacting an alkenethiophosphonic acid with DMP is:

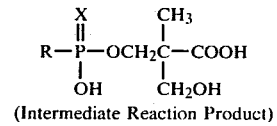

(Intermediate Reaction Product)

When this intermediate reaction product is reacted with, for example, diethylenetriamine, the following compound is representative of the principal final product:

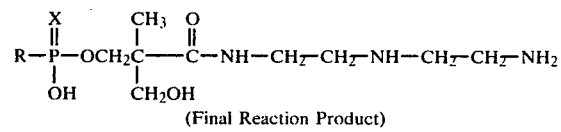

(Final Reaction Product)

Polyamines which can be employed as the amine reactant include alkene polyamines, such as ethylenediamine, proplyenediamine, butylenediamine, diethylenetriamine, triethylenetetramine, tetraethylenepentamine, pentaethylenehexamine, dipropylenetriamine, trimethylenediamine, tetramethylenediamine, pentamethylenediamine, hexamethylenediamine, and the like.

The amine reactant for producing the reaction product of the invention may also be a substituted amine reactant, e.g., an alkanolamine. Hydroxy-substituted amines which can be employed include ethanolamine, propanolamine, butanolamine, diethanolamine, and the like.

Polyols useful as the polyol reactants include triols, e.g., glycerol, trimethylolpropane; tetritols, e.g., pentaerythritol; pentitols, and hexatols, e.g., mannitol, sorbitol.

EXAMPLE 1

Preparation of Alkenethiophosphonic Acid

A polyisobutylene having an average molecular weight of approximately 1290 is reacted with phosphorus pentasulfide at a temperature of about 230° C. in the presence of free sulfur and a low viscosity paraffinic lubricating oil base stock (100E Pale Oil HF, a hydrogen-finished vacuum distillate fraction having typically a SUS viscosity of 96–104 and an API Gravity of 27–31 as diluent of the resulting olefin/$P_2S_5$ reaction product was hydrolyzed with steam and extracted with methanol to remove inorganic acids of phosphorus and low molecular weight organic acids of phosphorus. This purified reaction product, after stripping with nitrogen, has the following composition:

| | |
|---|---|
| Alkenethiophosphonic acid | 35 weight percent |
| 100 E Pale Oil HF | 58 weight percent |
| Unreacted polybutene | 7 weight percent |

It has the following inspection values:

| | |
|---|---|
| Neutralization Number | 17.3 |
| Sulfur, weight percent (Leco) | 1.07 |
| Phosphorus, weight percent (X-Ray) | 1.12 |

This is the alkenethiophosphonic acid starting material used in preparing the products of this invention. It is identified also as "Product A" in Table II, below, for comparison purposes:

EXAMPLE 2

Alkenethiophosphonic acid (ATPA), prepared as above described (Product A), was reacted with dimethylolpropionic acid to form a carboxylic acid intermediate product. Equimolar amounts of the mixture of ATPA, light mineral oil diluent, and unreacted polybutene resulting from the above-described preparation of alkenethiophosphonic acid, were reacted in xylene solvent by refluxing for 4 hours at 168° C. This product was tested for dispersancy in Bench VC Tests and is identified as "Product B" in Table II. It had the following inspection values:

| | |
|---|---|
| Neutralization Number | 10.0 |
| Phosphorus, weight percent (Leco) | 0.98 |
| Hydroxyl number | 9 |

EXAMPLES 3–4

Alkenethiophosphonic acid (ATPA), prepared as above-described, (Product A), was ethyoxylated, i.e., reacted with ethylene oxide and thereafter treated with $N_2O_4$. The final product is a commercial motor oil dispersant additive. Samples of the final product from two batches were tested by the Bench VC Test method as a basis for comparison with the product of this invention, and are identified as "Product C" and "Product D" in Table II, below. These products containing 0.89 and 1.06 weight percent phosphorus, respectively.

EXAMPLES 5–8

357 grams (0.1 M) of the mixture of alkenethiophosphonic acid (ATPA), diluent oil, and unreacted polybutene prepared as described above was reacted with 13 grams (0.1 M) dimethylolpropionic acid (DMP) in 150 ml. xylene at 168° C. for four hours to form the intermediate reaction product as described hereinabove. The product was cooled and stripped free of solvent to 135° C. at $2.6 \times 10^{-4}$ atm pressure. The resulting carboxylic acid intermediate reaction product was then reacted with equimolar amounts of various polyamines, alkanolamines or polyols at a temperature in the range of 185° to 190° C. for two to four hours in the presence of xylene solvent. Inspection values of the products are shown in Table I, below.

TABLE I

| | | Final Reaction Products | | | | |
|---|---|---|---|---|---|---|
| Ex. | Product | Intermediate* Reacted With: | % P | % S | Neut. No. | OH No. |
| 5 | E | Diethylenetriamine | 1.00 | 0.73 | 9.8 | 25 |
| 6 | F | Triethanolamine | 0.93 | 0.72 | 2.7 | 10 |
| 7 | G | Pentaerythritol | 1.01 | 0.89 | 4.7 | 29 |
| 8 | H | Aminopropylethylenediamine | 0.97 | 0.81 | 10.8 | 15 |

*The reaction product of dimethylolpropionic acid and alkenethiophosphonic acid.

The effectiveness of the various reaction products as lubricating oil dispersants was evaluated by the Bench VC Test (BVCT) on 7.5 weight percent blends of the various products in a base oil containing the following additives:

| Additive | Wt. % |
|---|---|
| Zinc dialkyldithiophosphate | 0.15 (as Zn) |
| Overbased calcium sulfonate 40 wt. % in 100 pale oil | 0.23 (as Ca) |
| Alkylated diphenylamine[1] | 0.28 |
| Polymethacrylate[2] | 0.56 |
| Ethylene-propylene copolymer[3] | 12.78 |

(1) A mixture of alkylated diphenylamine comprising approximately two-thirds 2,2'-diethyl-4,4'-tetriarydioctyldiphenylamine and one-third 2,2'-diethyl-4-tertiaryoctyldiphenylamine.

(2) The polymethacrylate serves as a pour depressant and is produced by reacting methacrylic acid with (a) a synthetic stearyl alcohol comprising up to 3% C-14 alcohol; 41+% C-16 alcohol; 32+% C-18 alcohol; and 14+% C-20 alcohol, and (b) laurylalcohol, a C-12 alcohol, to produce methacrylate monomers. (All alcohols are straight chain alcohols and all percentages are by weight). The monomers are copolymerized in the presence of azobisobutyronitile as catalyst with a small amount of lauryl mercaptan as modifier to a copolymer having a Saybolt Furol Seconds viscosity of 440° at 99° C.

(3) A copolymer of ethylene and propylene having a molecular weight of 20,000 to 50,000 containing 30 to 40 percent propylene in the copolymer in admixture with solvent neutral oil (100 E Pale Oil) comprising 13 weight percent copolymer and 87 weight percent oil. The base oil had the following properties:

| | |
|---|---|
| SUS Viscosity at 100° F. | 123–133 |
| SUS Viscosity at 210° F. | 53–55 |
| Viscosity Index, minimum | 95 |
| Gravity, API | 31.5–33.5 |

The Bench VC Test is conducted by heating the test oil mixed with synthetic hydrocarbon blowby and a diluent oil at a fixed temperature for a fixed period of time. After heating, the turbidity of the resulting mixture is measured. A low turbidity (0–10) is indicative of good dispersancy while higher BVCT numbers (20-100) are indicative of oils of increasingly poorer dispersancy.

Results of the Bench VC Test of the various products are shown in Table II.

TABLE II

| Dispersancy - Bench VC Test | | |
|---|---|---|
| Example | Product | BVCT at 7.5% |
| 1 | A | 72.0 |
| 2 | B | 27.0 |
| 3 | C | 13.0 |
| 4 | D | 16.0 |
| 5 | E | 3.5 |
| 6 | F | 2.5 |
| 7 | G | 4.0 |
| 8 | H | 5.5 |

With reference to the test results reported in Table II above, comparison of the reaction product (E, F, G, H) of this invention with other products including a commercial dispersant (C and D), indicate that the products of this invention have superior dispersant properties and are effective components to produce improved motor oil composition with low sludge and varnish-forming tendencies.

We claim:

1. An alkenethiophosphonic acid reaction product prepared by the process which comprises reacting an alkenethiophosphonic acid, in which the alkene radical has a molecular weight in the range of 400 to 20,000, and which contains the structural unit represented by the formula:

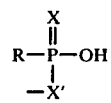

in which X and X' may be O or S and wherein an average of at least one is S, and R is an alkene radical derived from a monoolefinic polymer of similar molecular weight, with dimethylolpropionic acid in the presence of unreacted monoolefinic polymer and xylene solvent by refluxing about 168° C. to form a carboxylic acid intermediate product, and reacting said carboxylic acid intermediate product with diethylenetriamine at a temperature in the range of 185° to 195° C. to produce said reaction product.

2. An alkenethiophosphonic acid reaction product according to claim 1 in which said alkene radical has a molecular weight ranging from about 1050 to 1400.

3. A lubricating oil composition comprising a major proportion of a base oil of lubricating viscosity and a minor dispersant amount of an alkenethiophosphonic acid reaction product prepared by the process of claim 1.

* * * * *